United States Patent [19]

Moskowitz

[11] 4,447,536

[45] May 8, 1984

[54] STABILIZATION OF ENZYME COMPOSITIONS

[75] Inventor: Gerard J. Moskowitz, Mequon, Wis.

[73] Assignee: Dairyland Food Laboratories, Waukesha, Wis.

[21] Appl. No.: 436,638

[22] Filed: Oct. 25, 1982

[51] Int. Cl.³ .................. C12N 9/96; C12N 9/20; C12N 9/64

[52] U.S. Cl. .................. 435/188; 435/198; 435/226; 426/35

[58] Field of Search .............. 435/226, 188, 198; 426/35, 61, 63

[56] References Cited

U.S. PATENT DOCUMENTS 2,531,329 11/1950 Farnham ................ 426/35
2,794,743 6/1957 Farnham ................ 426/63

*Primary Examiner*—Lionel M. Shapiro
*Attorney, Agent, or Firm*—Michael, Best & Friedrich

[57] ABSTRACT

Enzyme-containing compositions made from gullets of young milk-fed animals and used to enhance the flavor and/or body consistency of cheeses are stabilized against loss of lipolytic activity by admixing therewith a stabilizing reagent comprising (a) at least 0.1 wt. % stannous chloride, (b) about 0.1 to about 1 weight % zinc chloride, or (c) at least 0.1 wt. % of one or more specific food acceptable divalent cationic salts and at least 0.05 wt. % of one or more food acceptable reducing agents, other than stannous chloride, capable of reacting with proteins without substantially denaturating them.

10 Claims, No Drawings

STABILIZATION OF ENZYME COMPOSITIONS

BACKGROUND OF THE INVENTION

This invention relates to stabilizing the activity of enzyme compositions and, more particularly, to stabilizing enzyme-containing compositions derived from so-called gullets of milk-fed animals.

One well recognized method for preserving enzyme-containing compositions against loss of activity during storage is to dry the composition. U.S. Pat. No. 2,794,743 describes an enzyme-containing composition in dry powder form prepared by grinding the edible tissue from between the tongue and trachea of young ruminants, such as calves, kids and lambs. Although dried to a low moisture content, such compositions have been found to lose their lipolytic activity during storage even though stored under refrigeration. Over a period of several weeks, dried enzyme-containing compositions made from calf tissue can lose up to as much as 40% of their initial activity. Dried enzyme-containing compositions made from kid and lamb tissue are also relatively unstable, although less unstable than those made from calf tissue.

The above enzyme-containing compositions are added to cheeses to promote ripening or aging and thereby produce desirable flavor and body consistency characteristics. The flavor and/or body consistency of some cheeses, particularly rapidly ripening cheddar cheeses, is highly dependent on the lipolytic activity of the enzyme-containing composition. In the production of such cheeses, a cheese maker typically assays a batch of the enzyme-containing composition and, based on the measured activity, determines the quantity of the enzyme-containing composition required for a given amount of cheese to produce the desired flavor and body consistency. The cheese maker thereafter continues to use the same amount of the enzyme-containing composition for the entire batch. A significant loss in the lipolytic activity over the period of time a batch of the enzyme-containing composition is being used can produce an unacceptable change in the flavor and/or body consistency of the final cheese product.

The loss of lipolytic acitivity can be minimized by vacuum packing the enzyme-containing composition. In addition to the added cost for packaging, the enzyme-containing composition tends to rapidly lose its activity upon opening of the package. This may not be particularly disadvantageous for applications where the enzyme-containing composition is used immediately after the package is opened. However, for applications requiring the enzyme-containing composition to be formulated with other materials prior to use or for operations where it takes several weeks to use up a batch of the enzyme-containing composition, the loss of activity during the time from package opening to actual use can create the above-mentioned problem.

SUMMARY OF THE INVENTION

One of the principal objects of the invention is to provide a low cost, effective method for stabilizing enzyme-containing compositions against a loss of lipolytic activity during storage.

Another of the principal objects of the invention is to provide a method for producing a stabilized enzyme-containing composition which does not require special packaging or storage conditions other than normal refrigeration.

A further of the principal objects of the invention is to provide a powdered enzyme-containing composition made from edible tissue taken from between the base of the tongue and the trachea of young ruminants and stabilized to minimize loss of lipolytic activity during storage.

Other objects, aspects and advantages of the invention will become apparent to those skilled in the art upon reviewing the following detailed description and the appended claims.

According to the invention, the lipolytic activity of enzyme-containing compositions prepared by grinding edible tissue taken from between the base of the tongue and the trachea of young ruminants and drying the ground tissue to remove a substantial portion of the moisture therefrom are stabilized by admixing with the ground tissue a stabilizing reagent comprising (a) at least 0.1 weight % stannous chloride, (b) about 0.1 to about 1 weight % zinc chloride, or (c) at least about 0.1 weight % of one or more of a certain class of food acceptable divalent cationic salts and at least about 0.05 weight % of one or more food acceptable reducing agents, other than stannous chloride, capable of reacting with proteins without causing substantial denaturation thereof.

In a preferred embodiment, the stabilizing reagent is an aqueous solution of a divalent cationic salt and a reducing agent and is added to the tissue during grinding in order to enhance homogeneous dispersion throughout the tissue and thereby maximize reaction of the stabilizing reagents with the enzymes.

DESCRIPTION OF THE PREFERRED EMBODIMENTS

The invention is particularly suitable for stabilizing enzyme-containing composition made from the glands defined in U.S. Farnham U.S. Pat. No. 2,531,329 against loss of lipolytic activity. These glands prefereably are processed in the manner described in Farnham U.S. Pat. No. 2,794,743 to produce a enzyme-containing composition in powdered form. Both of the above Farnham patents are incorporated herein by reference.

As mentioned above, these enzyme-containing compositions are added to cheeses to promote ripening or aging and produce desirable flavor and body consistency. As also mentioned above, loss of lipolytic activity in enzyme-containing compositions used in making rapidly ripening cheddar is particularly undesirable. The invention is most useful in stabilizing such compositions.

Generally, the glands or so-called gullets used as the starting material may be defined as the edible tissue taken from between the base of the tongue and the trachea of young ruminants, such as calves, kids and lambs.

The glandular tissue is ground to a size to pass through ¼ to ½ inch openings in a suitable meat grinder. The ground tissue is then thoroughly mixed with about 5 to about 25 weight % of sodium chloride to inhibit bacterial action.

About 0.8 to about 1.0 weight equivalents of nonfat dry milk or another suitable low-fat, milk-derived material, such as casein, are added to and thoroughly mixed with the ground and salted tissue to obtain a homogeneous mixture thereof. The nonfat dry milk serves as a diluent to facilitate future drying and grinding to a small particle size. Use of nonfat dry milk or a similar milk-derived material minimizes the amount of non-protein solids in the resulting enzyme composition.

The resulting mixture is then chopped in a hammermill or the like for further mixing of the tissue and milk powder and to break up agglomerated masses. In some cases, it may be advantageous to add more milk powder to the mixture prior to this chopping step in order to produce a product which can be conveniently separated for drying.

The chopped mixture is dried at a temperature below about 45° C., under either atmospheric or vacuum conditions, for a time sufficient to reduce the moisture content to about 7 weight % or less. This drying step usually takes about 24 to about 48 hours when performed under average atmospheric conditions and up to about 24 hours when performed under vacuum conditions.

The dried mixture of tissue and milk powder is pulverized in a suitable grinder to a size of about 40 to about 50 mesh.

In accordance with the invention, the resulting enzyme-containing composition is stabilized against loss of lipolytic activity by admixing with the ground tissue a stabilizing reagent comprising (a) stannous chloride, (b) zinc chloride or (c) one or more food acceptable divalent cationic salts and one or more food acceptable reducing agents. Many food acceptable divalent cationic salts by themselves do not provide an appreciable improvement in stability and, in some cases, actually cause an increase in the loss of lipolytic activity. However, when specific divalent cationic salts are used in combination with a reducing agent, the loss of lipolytic activity is reduced sigificantly. Likewise, many reducing agents by themselves provide little or no improvement in stability, but produce a significant improvement when combined with divalent cationic salts.

Suitable divalent cationic salts include calcium chloride, calcium carbonate, calcium orthophosphate in the mono, di or tri form, calcium oxide, calcium hydroxide, calcium sulfite, calcium salts of organic acids (e.g. calcium glutonate, calcium acetate, calcium glutamate and calcium lactate) zinc chloride, zinc carbonate, zinc acetate, zinc oxide, zinc sulfide, stannous chloride, titanium dioxide and mixtures of two or more of these salts. Zinc chloride can be used by itself or in combination with one or more reducing agents and/or other of the above divalent cationic salts. At present, the preferred divalent cationic salts are calcium chloride, calcium carbonate, zinc chloride and stannous chloride. Other divalent salts such as magnesium chloride, manganese chloride, and calcium sulfate, and monovalent salts, such as ammonium chloride, generally are not effective as stabilizers even though used in combination with one or more reducing agents.

The amount of divalent cationic salt used, other than zinc chloride, should be at least about 0.1 weight %, preferably about 3 to about 10 weight %, based on the total weight of the ground tissue. Amounts less than about 0.1 weight % do not provide an appreciable improvement in stability. While amounts in excess of about 10 weight % can be used, the small degree of improvement in stability usually is outweighted by the added cost.

When used alone, the amount of zinc chloride is about 0.1 to about 1 weight %. When used in combination with other divalent cationic salts, the total amount of such salts, including zinc chloride, should be at least about 0.1 weight % and can be up to 10 weight % or more so long as the amount of zinc chloride does not exceed about 1 weight %.

The reducing agent can be any food acceptable substance which is capable of reacting with the proteins in the ground tissue and bring about a reduction of the proteins without causing a substantial denaturation of the proteins.

Suitable reducing agents include, cystein, zinc dithionite, sodium dithionite, sodium sulfide, sodium sulfite, sodium bisulfite, sodium metabisulfite, sodium thiosulfate, sodium ascorbate, sodium erythorbate, sodium hypophosphite, butylated hydroxyanisol (BHA), glutathione (GSH), ascorbic acid, ascorbyl palmitate, butylated hydroxymethylphenol, calcium ascorbate, dilauryl thiodipropionate, erythorbic acid, ethoxquin, gum quaiac, lecithin, potassium metabisulfite, potassium sulfite, propyl gallate, and tert-butylhydroxyquinone (TBHQ).

The amount of the reducing agent should be at least about 0.05 weight %, preferably about 0.3 to about 10 weight %, based on the weight of the ground tissue. Amounts less than about 0.05 weight % do not provide an appreciable improvement in stability. While amounts in excess of 10 weight % can be used, the small degree of improvement ususally is outweighed by the added cost.

At present, the preferred reducing agents are cystein, sodium sulfite, GSH, sodium dithionite, sodium bisulfite and sodium metabisulfite.

A particularly suitable stabilizing reagent for enzyme-containing compositions made from calf gullet contains about 3 wt. % calcium chloride and about 0.3 wt. % sodium sulfite.

Stannous chloride is both a divalent cationic salt and a reducing agent within the meaning of those terms as used herein. Accordingly, it can be used by itself so long as the minimum amount is about 0.1 weight %, based on the weight of the ground tissue. It can also be used in combination with one or more reducing agents and other divalent cationic salts if desired.

The stabilizing reagents can be added to the ground tissue at different stages of processing, so long as the salt and reducing agent are dispersed throughout and intimately contact the tissue, thereby insuring their reaction with the enzyme to provide the desired stabilization. The stabilizing reagents preferably are added to the tissue as an aqueous solution containing the salt and reducing agent at the desired concentrations after the tissue has been ground and salted and before the tissue is mixed with nonfat dry milk. The mixture can be mixed and/or reground, after addition of such a solution in order to insure the uniform dispersion of the salt and reducing agent throughout the tissue.

Without further elaboration, it is believed that one skilled in the art can, using the preceding description, utilize the present invention to its fullest extent. The following examples are presented to exemplify the preferred embodiments of the invention and should not be constructed as limitations thereof.

In the examples, the same general procedure was employed in preparing enzyme-containing compositions from calf and kid gullets. Frozen gullets were thawed and portions were ground in a Hobart grinder along with 15 wt. % dendritic sodium chloride. The ground and salted tissue was transferred to a Hobart mixer and 0.9 weights of nonfat dry milk (NFDM) was added to and thoroughly mixed with the tissue. Some portions of the resulting mixture were used as controls and various divalent cationic salts, reducing agents and mixtures of the salts and reducing agents were added in an aqueous solution to other portions of the resulting mixture and mixed therewith in the Hobart mixer for about 10 minutes.

The thus-treated tissue was reground two times in the Hobart grinder to insure uniformed dispersion of the stabilizing reagents. 1-3 lb. samples of each portion was coated with approximately 0.5 lb. NFDM and manually chopped into small pieces. Each sample was placed in an aluminum drying pan and vacuum dried at a temperature of about 35°–38° C. for 18–20 hours. The dried samples were ground in a Weber laboratory grinder using a 0.24 mm perforated screen. After being assayed for lipolytic activity, each sample was placed in a plastic bag or screw cap bottle, stored at 4° C. and assayed weekly. The assays were performed in accordance with the method described in *Food Chemical Codex*, 3rd Edition, page 493, National Academic Press, Washington, D.C. (1981).

EXAMPLE 1

A series of test was run to determine the effect of various reducing agents, a divalent cationic salt ($CaCl_2$) and combinations of reducing agents and a divalent cationic salt on the stability of an enzyme-containing composition made from calf gullets. The results of these tests are summarized in Table 1.

From these results, it can be seen that the combination of a reducing agent and a divalent cationic salt provided substantially better stability of the enzyme-containing composition than either a reducing or a divalent cationic salt alone.

TABLE 1

Effect of Various Reducing Agents and $CaCl_2$ on Stability of Calf Enzyme Composition

| Additive, Wt. % | % Initial Activity, Weeks | | | | | |
|---|---|---|---|---|---|---|
| | 1 | 2 | 3 | 4 | 5 | 6 |
| Control | 89.3 | 83.4 | 77.5 | 76.5 | 77.0 | — |
| 0.1 Cystein | 97.4 | 88.8 | 79.5 | 82.9 | 77.7 | — |
| 0.1 $Na_2SO_4$ | 90.2 | 94.4 | 80.0 | 84.6 | 80.0 | 70.6 |
| 0.1 $Na_2SO_3$ | 97.2 | 90.0 | 81.0 | 86.1 | 80.1 | 61.6 |
| 0.1 $Na_2S_2O_3$ | 75.0 | 79.7 | 73.0 | 73.2 | 70.0 | 61.8 |
| 1.0 $CaCl_2$ | 93.1 | 93.0 | 90.0 | 83.2 | 92.4 | — |
| 1.5 $CaCl_2$ | 95.0 | 77.8 | 86.0 | 79.0 | 96.7 | 84.0 |
| 0.1 $Na_2S_2O_4$ + 1.0 $CaCl_2$ | 102.0 | 100.0 | 91.0 | 100.0 | 102.0 | 96.8 |
| 0.1 $Na_2SO_3$ + 1.0 $CaCl_2$ | 105.0 | 103.0 | 105.0 | 105.9 | 106.6 | — |
| 0.1 Cystein + 1.0 $CaCl_2$ | 106.0 | 110.0 | 104.0 | 98.1 | 105.3 | — |

EXAMPLE 2

A series of tests was run to determine the combined effect of a divalent cationic salt (1.0 wt. % $CaCl_2$) and various reducing agents on the stability of an enzyme-containing composition made from calf gullets. The results from those tests are summarized in Table 2.

From these results, it can be seen that the combination of a divalent cationic salt and a reducing agent enhanced the stability of the enzyme-containing composition throughout the 8-week test period. Two of the reducing agents, sodium dithionite and sodium thiosulfate, were effective during the first six weeks, but began to lose their ability to stabilize by the seventh week.

TABLE 2

Effect of Combinations of 1.0 Wt. % $CaCl_2$ and Various Reducing Agents on Calf Enzyme Composition

| Reducing Agent, Wt. % | % Initial Activity, Weeks | | | | | | | |
|---|---|---|---|---|---|---|---|---|
| | 1 | 2 | 3 | 4 | 5 | 6 | 7 | 8 |
| None (Control) | 97.5 | 97.1 | 93.9 | 84.8 | 87.1 | 77.8 | 70.8 | 67.3 |
| 2 GSH | 102.6 | 96.8 | 96.0 | 99.5 | 93.0 | 93.0 | 93.4 | 80.3 |
| 0.5 BHA | 104.3 | 103.2 | 97.1 | 97.2 | 93.7 | 89.4 | 87.0 | 84.4 |
| 0.1 Cystein | 101.1 | 96.3 | 96.3 | 97.9 | 91.0 | 97.9 | 86.1 | 83.0 |
| 0.1 $Na_2S_2O_2$ | 100.4 | 101.9 | 96.5 | 94.2 | 88.0 | 90.1 | 77.1 | 69.3 |
| 0.1 $N_2S_2O_3$ | 100.9 | 100.9 | 96.1 | 93.1 | 87.3 | 85.6 | 73.8 | 70.7 |
| 0.1 $Na_2SO_3$ | 105.1 | 103.6 | 104.0 | 103.0 | 100.1 | 96.1 | 86.7 | 87.7 |
| 0.1 $Na_2SO_2$ | 100.4 | 98.8 | 95.4 | 92.1 | 89.4 | 95.3 | 98.8 | 79.2 |

EXAMPLE 3

A series of tests was run to determine the combined effect of a reducing agent (0.1 wt % cystein) and various divalent cationic salts on the stability of an enzyme-containing composition made from calf gullets. Since stannous chloride is both a reducing agent and a divalent cationic salt, it was used by itself in the tests. Also, zinc chloride was used by itself. The results of these tests are summarized in Table 3.

From these results, it can be seen that a combination of a reducing agent and certain divalent cationic salts, namely, calcium sulfate, magnesium chloride, and manganese chloride and the combination of a reducing agent and a monovalent salt, ammonium chloride, are not effective in stabilizing the enzyme-containing composition. Also, it can also be seen that stannous chloride and zinc chloride are effective stabilizers by themselves.

TABLE 3

Effect of Combinations of 0.1 Wt. % Cystein and Various Divalent Cations on Calf Enzyme Composition

| Cation, Wt. % | % Initial Activity, weeks | | | | | | | |
|---|---|---|---|---|---|---|---|---|
| | 1 | 2 | 3 | 4 | 5 | 6 | 7 | 8 |
| Control | 90.4 | 87.0 | 82.4 | 80.6 | 69.5 | 71.8 | 67.2 | 62.6 |
| Cystein alone | 97.4 | 92.0 | 81.6 | 81.7 | 76.0 | 75.1 | 66.8 | 65.0 |
| 1 $CaCl_2$ | 97.5 | 97.1 | 93.9 | 84.8 | 87.1 | 77.8 | 70.8 | 67.3 |

TABLE 3-continued

Effect of Combinations of 0.1 Wt. % Cystein
and Various Divalent Cations on Calf Enzyme Composition

| Cation, | % Initial Activity, weeks | | | | | | | |
|---|---|---|---|---|---|---|---|---|
| Wt. % | 1 | 2 | 3 | 4 | 5 | 6 | 7 | 8 |
| 1 CaCO$_3$ | 102.0 | 98.4 | 96.5 | 87.3 | 83.2 | 77.9 | 68.9 | 70.7 |
| 1 CaSO$_4$ | 104.3 | 96.3 | 91.1 | 79.3 | 72.3 | 65.1 | 62.7 | 62.7 |
| 1 MgCl$_2$ | 101.5 | 98.9 | 91.1 | 84.4 | 74.3 | 68.1 | 59.7 | 61.6 |
| 1 MnCl$_2$ | 93.1 | 93.2 | 83.0 | 72.3 | 66.5 | 57.1 | 48.0 | 44.4 |
| 1 NH$_4$Cl | 108.8 | 97.7 | 86.1 | 80.0 | 76.0 | 71.0 | 61.9 | 60.9 |
| 1 TiO$_2$ | 104.7 | 101.4 | 92.8 | 93.8 | 81.9 | 74.8 | 63.9 | 65.9 |
| 0.1 SnCl$_2$[(1)] | 95.6 | 96.0 | 96.0 | 91.3 | 82.7 | 88.0 | 83.8 | 84.6 |
| 0.5 SnCl$_2$[(1)] | 106.2 | 103.2 | 97.1 | 103.2 | 105.0 | 89.7 | 85.6 | 86.7 |
| Control | 86.7 | 94.9 | 86.0 | 82.8 | 86.8 | 78.8 | 70.6 | 76.8 |
| 0.3 ZnCl$_2$ | 110.9 | 111.4 | 100.8 | 102 1 | 110.9 | 102.1 | 90.1 | 105.5 |

[(1)]SnCl$_2$ alone without cystein

EXAMPLE 4

A series of tests was run to determine the effect of combinations containing a constant amount of a divalent cationic salt (3.0 wt. % CaCl$_2$) and varying amounts of a reducing agent (Na$_2$SO$_3$) on the stability of an enzyme-containing composition made from calf gullets. The results of these tests are summarized in Table 4.

From these results, it can be seen that combinations containing concentrations of a reducing agent as low as about 0.05 wt. % are effective in stabilizing an enzyme-containing composition. Also, it can be seen that concentrations of a reducing agent up to 10 wt. % or higher can be used.

TABLE 4

Effect of Combinations of 3 Wt. % CaCl$_2$ and
Varying Concentrations of Na$_2$SO$_3$ on Calf Enzyme Composition

| Na$_2$SO$_3$, | % Initial Activity, Weeks | | | | | | | |
|---|---|---|---|---|---|---|---|---|
| Wt. % | 1 | 2 | 3 | 4 | 5 | 6 | 7 | 8 |
| Control | 94.6 | 73.5 | 79.7 | 77.6 | 77.6 | 78.3 | 79.0 | 68.1 |
| 0.03 | 81.1 | 78.3 | 73.7 | 61.0 | 66.2 | 62.1 | 67.3 | 54.6 |
| Control | 86.7 | 94.9 | 86.0 | 82.8 | 86.8 | 78.8 | 70.6 | 76.8 |
| 0.06 | 100.0 | 100.0 | 98.1 | 107.8 | 97.5 | 95.1 | 84.3 | 83.8 |
| Control | 94.6 | 73.5 | 79.7 | 77.6 | 77.6 | 78.3 | 79.0 | 68.1 |
| 0.3 | 88.9 | 67.6 | 84.5 | 83.7 | 82.9 | 82.9 | 91.4 | 81.2 |
| 3.0 | 87.0 | 72.9 | 96.2 | 93.3 | 87.1 | 85.4 | 79.1 | 78.0 |
| 10.0 | 93.1 | 83.6 | 87.9 | 86.6 | 88.3 | 88.3 | 86.7 | 87.4 |

EXAMPLE 5

A series of tests was run to determine the effect of combinations containing a constant concentration of a reducing agent (0.3 wt. % Na$_2$SO$_3$) and varying amounts of a divalent cationic salt (CaCl$_2$) on the stability of an enzyme-containing composition made from calf gullets. The results of these tests are summarized in Table 5.

From these results, it can be seen that combinations containing concentrations of a divalent cationic salt as low as about 0.1 wt. % are effective in stabilizing a enzyme-containing composition. Also, it can be seen that concentrations of the divalent cationic salt up to 10 wt. % or higher are effective.

TABLE 5

Effect of Combinations of 0.3 Wt. % Na$_2$SO$_3$ and
Varying Concentrations of CaCl$_2$ on Calf Enzyme Composition

| CaCl$_2$, | % Initial Acitivty, Weeks | | | | | | | |
|---|---|---|---|---|---|---|---|---|
| Wt. % | 1 | 2 | 3 | 4 | 5 | 6 | 7 | 8 |
| Control | 94.6 | 73.5 | 79.7 | 77.6 | 77.6 | 78.3 | 79.0 | 68.1 |
| 0.1 | 100.0 | 86.6 | 92.0 | 92.0 | 87.1 | 87.1 | 94.0 | 77.7 |
| 3.0 | 89.1 | 87.7 | 78.0 | 81.5 | 80.1 | 82.9 | 83.3 | 69.8 |
| 10.0 | 94.4 | 69.7 | 83.9 | 88.7 | 91.4 | 85.8 | 82.0 | 77.5 |
| Control | 89.0 | 78.1 | 76.6 | 79.0 | 75.1 | 66.7 | 70.9 | 62.3 |
| 1.0 | 96.6 | 94.2 | 96.3 | 86.7 | 86.7 | 84.4 | 81.5 | 74.9 |

EXAMPLE 6

A series of tests was run to determine the effect of a reducing agent (Na$_2$SO$_3$), a divalent cationic salt (CaCl$_2$) and a combination of the two on the stability of an enzyme-containing composition made from kid gullet. The results of these tests are summarized in Table 6.

TABLE 6

Effect of Na$_2$SO$_3$ and CaCl$_2$
on Kid Enzyme Composition

| Additive, | % Activity, Weeks | | | | | | | |
|---|---|---|---|---|---|---|---|---|
| Wt. % | 1 | 2 | 3 | 4 | 5 | 6 | 7 | 8 |
| Control | 105.5 | 99.4 | 95.1 | 93.2 | 82.9 | 97.5 | 82.2 | 82.7 |
| 0.6 Na$_2$SO$_3$ | 108.4 | 97.0 | 94.0 | 100.0 | 102.4 | 98.2 | 99.4 | 92.2 |
| 5.0 CaCl$_2$ | 72.1 | 89.5 | 85.5 | 79.1 | 85.5 | 91.9 | 80.2 | 79.1 |
| 0.6 Na$_2$SO$_3$ + 5.0 CaCl$_2$ | 120.6 | 121.3 | 105.0 | 113.5 | 92.1 | 101.4 | 97.9 | 100.0 |

From these test results, it can be seen that a combination of a reducing agent and a divalent cationic salt produces substantially better stabilization of an enzyme-containing composition that either alone.

From the foregoing description, one skilled in the art can easily ascertain the essential characteristics of the invention and, without departing from the spirit and scope thereof, make various changes and modifications to adapt it to various usages.

I claim:

1. In a method for making an enzyme-containing composition including the steps of grinding edible tissue taken from between the base of the tongue and the trachea of young ruminants and drying the mixture to remove a substantial portion of the moisture therefrom, the improvement comprising
   admixing with the ground tissue a stabilizing reagent comprising (a) at least 0.1 weight % stannous chloride, (b) about 0.1 to about 1.0 weight % zinc chloride, or (c) at least 0.1 weight % of a divalent cationic salt selected from the group consisting of calcium chloride, calcium carbonate, calcium orthophosphate in mono, di or tri form, calcium oxide, calcium hydroxide, calcium sulfite, calcium salts of organic acids, zinc chloride, zinc carbonate, zinc acetate, zinc oxide, zinc sulfite, stannous chloride, titanium dioxide and mixtures thereof and at least 0.05 weight % of a food acceptable reducing agent, other than stannous chloride, capable of reacting with proteins without causing substantial denaturation thereof, said weight percentages being based on the weight of the ground tissue.

2. A method according to claim 1 wherein the amount of said divalent cationic salt, other than zinc chloride, is about 3 to about 10 weight %.

3. A method according to claim 1 wherein said divalent cationic salt is calcium chloride, calcium carbonate or stannous chloride.

4. A method according to claim 1 wherein the amount of said reducing agent is about 0.3 to about 10 weight %.

5. A method according to claim 1 wherein said reducing agent is sodium sulfite, cystein, sodium dithionite, gluthathione, sodium bisulfite or sodium metabisulfite.

6. A method according to claim 1 wherein said stabilizing reagent is added to the ground tissue as an aqueous solution.

7. A method according to claim 6 wherein the ground tissue, prior to drying, is mixed with nonfat dry milk and the stabilizing reagent is added to the ground tissue prior to mixing with nonfat dry milk.

8. A method according to claim 1 wherein the tissue is taken from calves and the stabilizing reagent is an aqueous solution of calcium chloride and sodium sulfite.

9. A method according to claim 8 wherein the amount of calcium chloride and sodium sulfite is about 3 and about 0.3 weight %, respectively.

10. A stabilized enzyme-containing composition made by the method of claim 1.

* * * * *